US010806164B2

United States Patent
Arellano et al.

(10) Patent No.: US 10,806,164 B2
(45) Date of Patent: Oct. 20, 2020

(54) ADSORBENT OF MICOTOXINS BASED ON A BETAINE DERIVATIVE FOR BALANCED ANIMAL FOODS

(71) Applicant: Nutek, S.A. DE C.V., Tehuacán, Puebla (MX)

(72) Inventors: Lara Arellano, Puebla (MX); Garcia Rosas, Puebla (MX)

(73) Assignee: Nutek S.A. DE C.V., Tehuacan, Puebla (MX)

( * ) Notice: Subject to any disclaimer, the term of this patent is extended or adjusted under 35 U.S.C. 154(b) by 16 days.

(21) Appl. No.: 16/311,340

(22) PCT Filed: Jan. 5, 2017

(86) PCT No.: PCT/IB2017/050037
§ 371 (c)(1),
(2) Date: Dec. 19, 2018

(87) PCT Pub. No.: WO2017/221079
PCT Pub. Date: Dec. 28, 2017

(65) Prior Publication Data
US 2019/0191739 A1    Jun. 27, 2019

(30) Foreign Application Priority Data

Jun. 22, 2016   (MX) .................... MX/a/2016/008358

(51) Int. Cl.
| | |
|---|---|
| A23K 20/142 | (2016.01) |
| A23K 50/70 | (2016.01) |
| C07C 229/10 | (2006.01) |
| B01J 20/22 | (2006.01) |
| A23K 50/75 | (2016.01) |
| B01J 39/17 | (2017.01) |
| C07C 229/12 | (2006.01) |

(52) U.S. Cl.
CPC ............ *A23K 20/142* (2016.05); *A23K 50/70* (2016.05); *A23K 50/75* (2016.05); *B01J 20/22* (2013.01); *B01J 39/17* (2017.01); *C07C 229/10* (2013.01); *C07C 229/12* (2013.01)

(58) Field of Classification Search
None
See application file for complete search history.

(56) References Cited

U.S. PATENT DOCUMENTS 7,615,524 B2 * 11/2009 Del Duca ............ C11D 3/0015
510/296

FOREIGN PATENT DOCUMENTS

| CN | 103964456 A | * | 8/2014 |
|---|---|---|---|
| MX | 2007008369 | | 2/2009 |
| RU | 2391975 | | 6/2010 |
| WO | 02/07875 | | 1/2002 |
| WO | 2015/075686 | | 5/2015 |

OTHER PUBLICATIONS

Lu et al. CN103964456A_MT (Year: 2014).*
Lu et al., CN103964456A_MT, (Aug. 6, 2014). Machine Translated version of Chinese Application. (Year: 2014).*
International Search Report dated Apr. 19, 2017, based on co-pending PCT Application No. PCT/IB2017/050037, 3 Pages.
Written Opinion dated Apr. 19, 2017, based on co-pending PCT Application No. PCT/IB2017/050037, 5 Pages.
Wu et al., Synthesis of SAPO-56 with controlled crystal size, J. Nanopart. Res. 19:93 (2017).
Sun et al., The state-of-the-art synthetic strategies for SAPO-34 zeolite catalysts in methanol-to-olefin conversion, Natl. Sci. Rev. 5:542-58 (2018).
Doan et al., Synthesis of SAPO-34 using different combinations of organic structure-directing agents, Hindawi J. Chem. 2019:6197527 (2019).
Peyman et al., Effect of synthesis parameters on phase purity, crystallinity and particle size of SAPO-34, Iran. J. Chem. Chem. Eng. 30:29-36 (2011).

* cited by examiner

*Primary Examiner* — Clinton A Brooks
*Assistant Examiner* — Kofi Adzamli
(74) *Attorney, Agent, or Firm* — McCarter & English, LLP

(57) ABSTRACT

The present invention provides a mycotoxin adsorbent based on a highly specific betaine derivative for trichothecenes A and B, and especially for vomitoxin (or deoxynivalenol) and T-2 toxin; as well as a process for preparing said mycotoxin adsorbent. The mycotoxin adsorbent of the invention is obtained by modifying the surface of an aluminosilicate by means of an organic amphoteric compound with a carboxyl group that provides it with high polarity properties. The mycotoxin adsorbent is useful for preparing balanced feed from animals that avoid the toxic effects of mycotoxins.

19 Claims, No Drawings

ADSORBENT OF MICOTOXINS BASED ON A BETAINE DERIVATIVE FOR BALANCED ANIMAL FOODS

CROSS-REFERENCE TO RELATED APPLICATIONS

This application is a national stage application filed under 35 USC 371 of PCT/IB2017/050037, filed Jan. 1, 2017, which claims the benefit of Mexican Patent Application No. MX/a/2016/008358, filed Jun. 22, 2016, each of which is incorporated herein, in its entirety, by reference.

TECHNICAL FIELD OF THE INVENTION

The present invention relates to the technical field of mycotoxin adsorbents that are used in balanced foods to avoid the harmful effects of type A and B trichothecenes, with special emphasis on vomitoxin (or deoxynivalenol) and T-2 toxin in animals. Also, this invention relates to a premix for preparing a mycotoxin adsorbent, an additive for balanced animal feed or a balanced feed formulation for animals that includes said mycotoxin adsorbent; and the use of said mycotoxin adsorbent in the preparation of an additive for animal feed to treat or prevent one or more deleterious effects or symptoms in the digestive tract associated with trichothecene intoxication.

BACKGROUND

Mycotoxins are chemical compounds of low molecular weight produced by fungi, which have pathological effects in both humans and animals. There are hundreds of mycotoxins that are produced by various fungi that contaminate grains and food either in the field or in storage silos. In the field, the fungus that most commonly affects the grains is *Fusarium* sp that produces the toxins zearalenone, fumonisin and trichothecenes, for example vomitoxin, T-2 toxin or diacetoxyscirpenol (DAS), among others.

Particularly, trichothecenes are mycotoxins produced mainly by several species of fungi of the *Fusarium* genus (eg *F. Sporotrichioides, F. graminearum, F. poae* and *F. culmorum*) and can be produced by members of other genera, such as: *Myrothecium, Cephalsporium, Trichoderma* and *Trichothecium*. The trichothecenes are chemically characterized by the presence of a basic system of a tetracyclic ring of scirpenol.

Chemically, trichothecenes are compounds that have sesquiterpene rings characterized by a 12,13-epoxy-9-tricothecene core, and have a variable number of substitutions with hydroxyl or acetoxy groups at positions 3, 4, 7, 8 and 15 of the molecule. Regularly, some trichothecenes only differ among themselves by a single acetyl group.

In total there are four groups of trichothecenes; however, the genus *Fusarium* only produces trichothecenes of type A and B. Considering that livestock interests are more focused on trichothecenes of the genus *Fusarium*, these two groups are of greatest interest.

Examples of type A trichothecenes are toxin T-2, toxin HT2, diacetoxyscirpenol (DAS) and neosolaniol, and among the most important type B trichothecenes are Deoxynivalenol (DON), better known as Vomitoxin, and Nivalenol.

The basic structure of trichothecenes is presented in formula (I) and the substitutions to this basic structure that form groups A and B are presented in table 1.

Formula (I)

Basic structure of trichothecenes

TABLE 1

Structure of group A and B trichothecenes.

| Trichothecenes | PM$^a$ | R$^1$ | R$^2$ | R$^3$ | R$^4$ | R$^5$ |
|---|---|---|---|---|---|---|
| Type A | | | | | | |
| Diacetoxyscirpenol (DAS) | 366 | OH | OAc | OAc | H | H |
| Toxin HT-2 (HT-2) | 424 | OH | OH | OAc | H | OCOCH$_2$CH(CH$_3$)$_2$ |
| Toxin T-2 (T-2) | 466 | OH | OAc | OAc | H | OCOCH$_2$CH(CH$_3$)$_2$ |
| Neosolaniol (NEO) | 382 | OH | OAc | OAc | H | OH |
| Type B | | | | | | |
| Deoxynivalenol (DON) | 296 | OH | H | OH | OH | O |
| 3-acetyl Deoxynivalenol (3-AcDON) | 338 | OAc | H | OH | OH | O |
| Nivalenol (NIV) | 312 | OH | OH | OH | OH | O |
| Fusarenon-X (Fus-X) | 354 | OH | OAc | OH | OH | O |
| Trichothexone (TRI) | 264 | H | OH | H | H | O |

$^a$Molecular Weight (g/mol), R1-R5 are expressed in Formula 1.

Regularly, trichothecenes produce the following harmful effects in animals: Vomiting, diarrhea, irritation, hemorrhages and necrosis in the digestive tract.

Particularly, the most potent mycotoxins of this group are the T-2 toxin and the diacetoxyscirpenol (DAS); oral lesions caused by these mycotoxins are characteristic in birds. On the other hand, the most prevalent trichothecene in grains and balanced foods, which is most frequently found in high concentration, is deoxynivalenol (DON) or vomitoxin, whose name derives from the fact that it produces vomiting and rejection of food by the animal. Pigs, especially, are very sensitive to the effects of trichothecenes.

Although the difference between the toxic effects of the T-2 toxin and vomitoxin (DON) is not very noticeable in terms of food consumption, both toxins notably differ in the rest of their toxic effects. The effects of these toxins are due to the fact that, in both cases, the levels of dopamine, tryptophan, serotonin and serotonin metabolites are altered in the brains of rodents and pigs (Prelusky et al 1992).

It has been observed that the concentration in the brain of these substances is altered in the same way that the anorexic substances do, which is why it has been suggested that the reduction in the consumption of food by the animals is due, at least in part, to the result of the alteration of neurotransmitter levels in the brain. It is also probable that in the future a relationship will be found between these toxic effects and the peripheral nervous system.

Considering the above, the industry has estimated that prevention is the best way to deal with the problem of mycotoxins in animal feed. For which, it has endeavored to have an adequate grain management program that reduces the possibility that grain, and food will become contaminated with these toxins. They have even tried to implement programs that prevent the already contaminated grains from reaching storage facilities.

Several ways of treating contaminated grain have already been investigated to obtain good quality grains; however, all these preventive measures have proved to be insufficient. In this regard, the Food and Agriculture Organization of the United Nations (FAO) has estimated that a large part of the world's grain is contaminated with mycotoxins and the reason for this observation is precisely due to the failure of the programs so far implemented in the Industry (Bhat and Vasanthi 1999).

One of the solutions that has been proposed to solve the problem of contamination with mycotoxins in animal feed is the use of mycotoxin adsorbents, which are used as additives in food, and work by trapping or adsorbing mycotoxins when they are found in the aqueous environment of the animal's gastrointestinal tract once said animal consumes the contaminated food. These mycotoxin adsorbents prevent, mainly, that the mycotoxins be absorbed by the animal, that they pass into the circulatory system and that they consequently cause their harmful effects.

The use of aluminosilicates, clays, zeolites and even organoaluminosilicates as mycotoxin adsorbents has already been known for several years (Phillips et al 1988, Kubena et al 1990).

In the state of the art, we find several documents that refer to mycotoxin adsorbents. For example, the international patent application with publication number WO 91/13555 published on Sep. 19, 1991, describes a solid, dry, biodegradable composition, coated with a sequestering agent, to be used as an additive to adsorb mycotoxins in contaminated food. Said composition comprises a phyllosilicate mineral such as calcium montmorillonite.

For its part, the document S. L. Lemke, P. G. Grant and T. D. Phillips "Adsortion of Zearalenone by Organophilic Montmorillonite Clay" J Agric. Food Chem. (1998), pp. 3789-3796, describes an organically modified montmorillonite clay (organophilic) which is capable of adsorbing zearalenone, wherein the organophil may be, inter alia, for example hexadecyltrimethylammonium (chloride), a quaternary amine that has methyl groups and a chain of sixteen aliphatic and linear carbons, but none of these radicals is polar.

The US patent with publication number U.S. Pat. No. 6,827,959 B1 published on Dec. 7, 2004 discloses mycotoxin adsorbents comprising an organically modified laminated silicate which comprises a quaternary onium compound, wherein said onium compound includes at least one $C_{10}$-$C_{22}$ alkyl group and an aromatic substituent, and wherein 2 to 30% of the interchangeable cations of the layered silicate are exchanged with quaternary onium compounds. The alkyl group of the quaternary onium compound of this mycotoxin adsorbent is an aliphatic but non-polar chain.

The international patent application with publication number WO 02/052950 (2002), which describes a modified organomineral with a long-chain quaternary amine, for example with dioctadecyltrimethylamine, octadecyltrimethylamine, octadecyldimethylamino and similar compounds, all of which are quaternary amines having methyl groups and an aliphatic and linear carbon chain, but no radical is polar. This modified organomineral is used as a feed additive to adsorb mycotoxins in animals.

The US patent application with publication number US 2004/0028678 A1 published on Feb. 12 2004, for its part, describes the use of an acid-activated laminated silicate to adsorb aflatoxins, ochratoxins, Fumonisin, zearalenone, deoxynivalenol, T-2 toxin and ergotamine.

The US patent application with publication number US 2008/0248155 (2008) describes the use of a composition comprising stevensite for the adsorption of mycotoxins, such as, for example, mycotoxin T-2.

The US patent application with publication number US 2010/0330235 (2010) describes a mycotoxin adsorbent, for example aflatoxin, zearalenone, ochratoxin A and fumonisin B1, based on the combination of an organic silicate with amorphous structure and dodecylamine, which is a primary amine that has a carbon chain of twelve carbons aliphatic and linear, but non-polar.

Recently, other solutions have also been proposed to solve the problem of food decontamination with mycotoxins. For example, US patent application US 2012/0070516 published on Mar. 22, 2012 discloses a method to render the food contaminated with mycotoxins less detrimental, such as deoxynivalenol and T-2 toxin, using basically plant lignocellulosic biomass or its isolated biomass components. We also find the US patent application US 2012/0219683 published on Aug. 30, 2012, which describes a mycotoxin adsorbent, such as deoxynivalenol and T-2 toxin, which comprises a material of clay and activated carbon to decontaminate the food with undesirable mycotoxins.

On the other hand, the International patent application with publication number WO 2015/075686, presents an adsorbent of the organoaluminosilicate type using a quaternary ammonium group functionalized with an ethoxylated alkyl phenol chain or more particularly a derivative of an ethoxylated nonyl phenol, and the derived mycotoxin adsorbent presents good protection against the toxic effect of vomitoxin and T2 toxin.

Despite all the above efforts, in the technical field of the present invention there is still a need for alternatives to face the problem of mycotoxins, such as vomitoxin, T-2 toxin, aflatoxins and fumonisin B1, in animal feed.

BRIEF DESCRIPTION OF THE INVENTION

As a result of extensive research work, the inventors of the present application have found experimentally and unexpectedly that a mycotoxin adsorbent of the organoaluminosilicate type using a carboxyl functional group in one of the aliphatic chains of a quaternary ammonium compound, allows a high adsorption of vomitoxin and/or T-2 toxin, whose target value of adsorption of vomitoxin turns out to be particularly high, and also maintains the adsorption of other mycotoxins, such as aflatoxins, fumonisin B1.

In a first aspect, the present invention relates to a mycotoxin adsorbent of the organoaluminosilicate type which uses a quaternary ammonium compound with a carboxyl functional group in one of its aliphatic chains, which is used in balanced feeds to avoid the harmful effects of mycotoxins, particularly of type A and B trichothecenes, and with special emphasis on vomitoxin (or deoxynivalenol) and T-2 toxin in animals. It was found that the carboxyl group in the aliphatic radicals of the quaternary ammonium compound used in the aluminosilicate imparts a high polarity to the surface to the mycotoxin adsorbent of the present invention.

In a second aspect, the invention relates to a premix for preparing the mycotoxin adsorbent of the present invention, an additive for balanced animal feed and a balanced feed formulation for animals including the mycotoxin adsorbent of the invention.

In a third aspect, the invention relates to the use of the mycotoxin adsorbent of the present invention, in the preparation of an additive for animal feed and in the preparation of a balanced feed formulation, to treat or prevent one or more noxious effects or symptoms in the digestive tract associated with trichothecene poisoning, particularly trichothecenes A and B, and especially Vomitoxin (or Deoxynivalenol) and T-2 toxin.

In a fourth aspect, the present invention provides a process for preparing a trichothecene adsorbent especially for vomitoxin, by reacting a base aluminosilicate with a cation exchange capacity of at least 20 milliequivalents/100 g and an amphoteric organic compound having a group carboxyl at one end.

In a further aspect, the present invention relates to the use of the mycotoxin adsorbent of the invention in a food contaminated with mycotoxins. The invention is also directed to a method for preparing a balanced feed for animals that avoids the problems of mycotoxicosis in animals.

The mycotoxin adsorbent of the invention is used by adding it to the contaminated food, either in granular or powder form, either alone or in combination with a known mycotoxin adsorbent, in order to achieve a better adsorption of the mycotoxins, which are eliminated together through feces.

Thus, by means of the practice of the present invention, it is possible to avoid the absorption of mycotoxins in contaminated foods into the gastrointestinal tract of an animal, when the animal ingests its food and, consequently, thereby substantially improving the health of the animal, which is reflected both in the weight gain in the animal, and in the productivity of the derived products such as eggs or milk.

DETAILED DESCRIPTION OF THE INVENTION

The inventors of the present application experimentally explored the hypothesis of increasing the polarity of the surface of a mycotoxin adsorbent of the organoaluminosilicate type by using a carboxyl functional group in one of the aliphatic chains of a quaternary ammonium compound in order to efficiently adsorb the mycotoxins.

In this way, the present invention is based on the fact that a modification of the surface of the aluminosilicates by a treatment as described in the present application, can be used to increase its capacity for mycotoxin adsorption. The treatment to be followed depends on what is intended to be achieved, but generally two main characteristics of the surface are manipulated, which are the hydrophilic character and the hydrophobic or organophilic character (Lara et al 1998).

Particularly, in the present invention the modification of the surface is carried out with an organic amphoteric compound with a carboxyl functionality, in such a way that the surface achieves a highly polar character. The organic compound that is used for the modification of the surface may occupy part or all the active sites on the surface of the aluminosilicate.

The aluminosilicate used can be a tectosilicate or a phyllosilicate or a mixture of both, with the proviso that the material that is used has a cation exchange capacity of at least 20 milliequivalents per 100 grams of material, and preferably 55 milliequivalents per 100 grams of material.

The selection of the organic compound depends on the specificity and efficiency that is desired in the adsorption of mycotoxins. In the case of the present invention, preferably the organic compound used is a betaine (trimethylglycine or TMG). This organic compound is used in a proportion of 25% to 120% of the cation exchange capacity of the aluminosilicate used. The reaction is carried out in aqueous medium with stirring at a temperature between 15 and 85° C. and with a time of 0.25 to 3 hours. The product is separated by filtration, dried at a temperature between 40 and 150° C. and granulated or ground to meshes between 100 and 325.

The additive object of the present invention is a low inclusion adsorbent that is added to foods contaminated with trichothecenes, at a ratio of 0.025% to 0.2% of the weight of the food.

According to the first aspect, the invention relates to a mycotoxin adsorbent characterized in that it comprises an organically modified aluminosilicate with a betaine derivative of general formula (I) or a salt of said derivative:

$$R-\overset{\overset{CH_3}{|}}{\underset{\underset{CH_3}{|}}{N^{\oplus}}}-[CH_2]_n-\overset{O}{\underset{}{\overset{\|}{C}}}-O^{\ominus} \quad (I)$$

wherein R represents an alkyl group with 1 to 12 carbon atoms and n is 1 to 12.

In the case that R is equal to 1 and n is equal to 1, the betaine derivative of formula (I) is trimethylglycine, known simply as Betaine, according to figure (Ia):

$$\underset{H_3C}{\overset{H_3C}{\underset{H_3C}{\searrow}}}\overset{\oplus}{N}\underset{}{\overset{}{\diagdown}}\overset{O}{\underset{O^{\ominus}}{\diagup}} \quad (Ia)$$

In one embodiment, the invention relates to a mycotoxin adsorbent characterized in that it comprises an organically modified aluminosilicate with a betaine derivative of formula (I) or a salt of said derivative, wherein the aluminosilicate can be a tectosilicate, a phyllosilicate or a mix of both.

In still another embodiment, the invention relates to a mycotoxin adsorbent characterized in that it comprises an organically modified aluminosilicate with a betaine derivative of formula (I), wherein R represents a methyl group and n is 1 to 12, more preferably n is 1 to 6, and more preferably n is equal to 1.

The invention also relates to a mycotoxin adsorbent characterized in that it comprises an organically modified aluminosilicate with a betaine derivative of formula (I), wherein n is equal to 1 and R represents alkyl with 1 to 6 carbon atoms, preferably R represents alkyl with 1 to 3 carbon atoms and more preferably R represents alkyl with 1 carbon atom.

Another additional particular embodiment, the invention relates to a mycotoxin adsorbent characterized in that it comprises an aluminosilicate organically modified with a salt of the betaine derivative of formula (I), preferably said salt is Betaine Hydrochloride according to formula (Ib):

$$\text{(Ib)}$$

In another embodiment, the mycotoxin adsorbent according to the invention comprises an aluminosilicate organically modified with the betaine derivative of formula (I) or a salt of said derivative, wherein the aluminosilicate has a cation exchange capacity of at least 20 milliequivalents per 100 grams of material and more preferably 55 milliequivalents per 100 grams of material.

The mycotoxin adsorbent according to the present invention may further comprise an aluminosilicate organically modified with the betaine derivative of formula (I) or a salt of said derivative, which is used in a proportion of 25% to 120% of the capacity of cation exchange (CEC) of the aluminosilicate used, preferably used in a proportion of 60% to 120% CEC.

In a further embodiment, the mycotoxin adsorbent according to the invention may comprise an aluminosilicate organically modified with the betaine derivative of formula (I) or a salt of said derivative, having a cation exchange capacity of at least 55 milliequivalents per 100 grams of material.

The invention also relates to a mycotoxin adsorbent comprising an aluminosilicate organically modified with the betaine derivative of formula (I), (Ia), or a salt of said derivative, particularly betaine hydrochloride having the formula (Ib), wherein said betaine derivative of formula (I) or the salt of said derivative, is used in a proportion of 25% to 120% of the cation exchange capacity (CEC) of the aluminosilicate used and more preferably is used in a proportion from 60% to 120% CIC.

According to the second aspect, the invention relates to a premix for preparing the mycotoxin adsorbent of the present invention, an additive for animal feed and a balanced feed formulation for animals including the mycotoxin adsorbent of the invention.

According to the third aspect, the invention relates to the use of the mycotoxin adsorbent of the present invention, in the preparation of an additive for balanced feed of animals and in the preparation of a formulation of a balanced feed, to treat or prevent one or more harmful effects or symptoms in the digestive tract associated with trichothecene poisoning, particularly trichothecenes A and B, and especially vomitoxin (or deoxynivalenol) and T-2 toxin.

The invention involves the use of a mycotoxin adsorbent characterized in that it comprises an organically modified aluminosilicate with a betaine derivative according to formula (I) or a salt of said derivative, in the preparation of an additive for animal feed to treat or prevent one or more deleterious effects or symptoms in the digestive tract associated with trichothecene A and/or B poisoning, such as vomiting, diarrhea, irritation, hemorrhages or necrosis in the digestive tract associated with trichothecene intoxication.

In the present invention, one or more deleterious effects or one or more symptoms in the digestive tract associated with trichothecene poisoning can be selected from the group consisting of: Diacetoxyscirpenol (DAS), HT-2 toxin (HT-2), T-2 toxin (T-2), neosolaniol (NEO), deoxynivalenol (DON) or vomitoxin, 3-acetyldeoxynivalenol (3-AcDON), nivalenol (NIV), fusarenon-X (Fus-X), trichotecolone (TRI) and a combination of the above.

Also, another embodiment of the invention relates to the use of an additive for animal feed in accordance with the invention in the preparation of a balanced feed formulation to reduce or eliminate the deleterious effects or symptoms in the digestive tract associated with the trichothecene intoxication in animals, specifically the harmful effects of trichothecenes A and/or B, and more specifically of deoxynivalenol (or vomitoxin) and T-2 toxin.

The invention also consists of a mycotoxin adsorbent according to the invention for use as an animal feed additive to treat or prevent one or more deleterious effects or one or more symptoms in the digestive tract associated with trichothecene poisoning, wherein the additive for animal fodder is to treat or prevent vomiting, diarrhea, irritation, hemorrhages, necrosis or oral lesions.

The present invention further relates to a process for preparing the mycotoxin adsorbent of the invention comprising the following steps:

a) contacting an aluminosilicate with cation exchange capacity of at least 20 milliequivalents per 100 grams of material in an aqueous medium with stirring at a temperature between 15 and 85° C. and with a time of 0.25 to 3 hours with a derivative of betaine of formula (I) or (Ia), or with a salt of said derivative, particularly hydrochloride of a betaine derivative of formula (Ib) and more particularly betaine hydrochloride, in a proportion of 25% to 120% of the cation exchange capacity of the aluminosilicate used;

b) Separate by filtration;

c) Dry at a temperature between 40 and 150° C.; and d) Granulate or grind to meshes between 100 and 325.

The following examples show that the objective value of protection against the effects of vomitoxin and T-2 toxin by the mycotoxin adsorbent of the present invention turns out to be particularly high. Said examples, which include the preparation of the mycotoxin adsorbent of the present invention and its "in vivo" evaluation, all of which is provided for the purpose of illustration and not limitation.

Example 1

Preparation of the Micotoxin Adsorbent of the Invention

Method with Betaine

Raw Materials to be Used.
The characteristics of the organic compound used for the surface treatment are shown in Table 2.
The base aluminosilicate used is an aluminosilicate of the Bentonite type, with cation exchange capacity of 55 meg/100 g.

TABLE 2

Characteristics of the betaine used.

| QUATERNARY | TYPE | STRUCTURE | MOLECULAR WEIGHT | LOAD |
|---|---|---|---|---|
| Betaine | Amphoteric Quaternary | (Ia) | 117 | +1 |

Formulation.

The initial experimental design was developed based on the substitution percentage of the cation exchange capacity (CEC) of the base aluminosilicate. A substitution percentage of 60% to 120% of CEC was taken as a base.

Experimental Development of Formulations.

Materials and Equipment.
1. Laboratory glassware
2. Magnetic stirrer.
3. Drying stove.
4. Mortar or laboratory mill.
5. 200 mesh screen.

Process.
The exchange procedure is carried out according to the state of the art (S L Lemke, P G Grant and T D Phillips "Adsortion of Zearalenone by Organophilic Montmorillonite Clay" J Agric. Food Chem. (1998), pp. 3789-3796). In this particular case, hydrochloric acid is added to the water in order to obtain a positive charge in the nitrogen.
The final phase of the reaction is carried out with a time of 2 hours.
Filter the mixture.
Dry the sample in the oven at a temperature of around 105° C.
Grind the sample.
Sieve in 200 mesh.
Carry out corresponding analyses according to the sample.

Example 2

Preparation of the Micotoxin Adsorbent of the Invention

Method with Betaine Hydrochloride

Raw Materials to be Used.
The characteristics of the organic compound used for the surface treatment are shown in Table 3.
The base aluminosilicate used is an aluminosilicate of the Bentonite type, with cation exchange capacity of 55 meq/100 g.

Formulation.

The initial experimental design was developed based on the substitution percentage of the cation exchange capacity (CEC) of the base aluminosilicate. A substitution percentage of 60% to 120% of CEC was taken as a base.

Experimental Development of Formulations.

Materials and Equipment.
6. Laboratory glassware
7. Magnetic stirrer.
8. Drying oven.
9. Mortar or laboratory mill.
10. 200 mesh screen.

Process.
The exchange procedure is carried out according to the state of the art (S L Lemke, P G Grant and T D Phillips "Adsortion of Zearalenone by Organophilic Montmorillonite Clay" J Agric. Food Chem. (1998), pp. 3789-3796). In this case, due to the hydrochloride in the betaine used, no hydrochloric acid is added.
The final phase of the reaction is carried out with a time of 2 hours.
Filter the mixture.
Dry the sample in the oven at a temperature of around 105° C.
Grind the sample.
Sieve in 200 mesh.
Carry out corresponding analyses according to the sample.

Example 3

"In Vivo" Evaluation in Rats with a Mycotoxin Adsorbent of the Invention Designed to Adsorb Vomitoxin (or Deoxynivalenol)

In this example it is used as an adsorbent of mycotoxins, an aluminosilicate organically modified with a betaine hydrochloride, which we call Zeotri B2 or ZB2.

In the experiment, 30 freshly weaned male Sprague Dawley rats distributed in 3 groups and with one week of adaptation were used. A single rat was used as a repetition.

TABLE 3

Characteristics of the betaine used.

| QUATERNARY | TYPE | STRUCTURE | MOLECULAR WEIGHT | LOAD |
|---|---|---|---|---|
| Betaine | Quaternary Amphoteric | (Ib) | 153.6 | +1 |

The negative and positive control groups as well as the challenge group had 10 rats per treatment. The rats were received from the bioterium of the Benemerita Autonomous University of Puebla (BUAP). The experimental time was 35 days. The level of contamination with Vomitoxin (or DON) was 12 mg/kg (12 ppm or 12,000 ppb) in the food. The Zeotri B2 adsorbent dose was 1.5 kg/Ton of feed.

The DON present in the feed affected the growth rate of the animal; this is observed in the weight gain due to the decrease in the consumption of the food.

At the used concentration of 12,000 ppb of DON, there were statistically significant differences in the productive parameters among the three treatments: weight gain, food consumption and feed conversion. An important observation is that the group treated with Zeotri B2 had less variation in the final weight and this is confirmed because there is less standard error.

The European Union states that a product is considered effective, based on a biomarker when it protects a 40%. In this case, the effectiveness was estimated based on the weight gain with respect to the positive control group, which is the weight recovered by the group that consumed the adsorbent. The effectiveness of the mycotoxin adsorbent of the present invention, based on the weight gain, was surprisingly ZB2=64.1%.

Tables 4 to 6 below show the productive results in initial and final weight, as well as weight gains, feed consumption and feed conversion.

TABLE NO. 4

Initial and Final Weights, Weight gain, Alimentary conversion and food consumption.

| | Weight in g | | | | |
|---|---|---|---|---|---|
| Treatments | Initial (21 days old) Means ± standard error | Final (56 días de edad) Means ± standard error | Weight gain Means ± standard error | Food conversion Means ± standard error | Food consumption Means ± standard error |
| Negative control | 108 ± 7.84 [a] | 256 ± 9.05 [a] | 148 ± 7.22 [a] | 4.51 ± 0.058 [a] | 666 ± 8.55 [a] |
| Positive Control DON | 100 ± 5.27 [a] | 209 ± 10.4 [b] | 109 ± 6.61 [b] | 5.22 ± 0.195 [b] | 569 ± 19.1 [b] |
| Challenge Zeotri B2 + DON | 97 ± 2.42 [a] | 231 ± 4.09 [ab] | 134 ± 2.94 [a] | 4.68 ± 0.045 [a] | 627 ± 5.99 [a] |

Averages with different letters are statistically significant for $p < 0.05$.

TABLE NO. 5

Weight gain during the experimental period

| Treatments | Gain of weight from 0 to 7 days Means ± standard error | Gain of weight from 7 to 14 days Means ± standard error | Gain of weight from 14 to 21 days Means ± standard error | Gain of weight from 21 to 28 days Means ± standard error | Gain of weight from 28 to 35 days Means ± standard error |
|---|---|---|---|---|---|
| Negative Control | 36 ± 2.84 [a] | 31 ± 0.84 [a] | 27 ± 3.02 [a] | 27 ± 1.73 [a] | 28 ± 1.87 [a] |
| Positive control DON | 24 ± 2.45 [b] | 24 ± 3.04 [a] | 21 ± 2.92 [a] | 13 ± 3.89 [b] | 27 ± 3.63 [a] |
| Challenge Zeotri B2 + DON | 28 ± 1.54 [ab] | 29 ± 1.21 [a] | 26 ± 2.75 [a] | 26 ± 3.66 [a] | 25 ± 2.30 [a] |

Averages with different letters are statistically significant for $p < 0.05$.

TABLE NO. 6

Food consumption during the experimental period.

| Treatments | Food consumption from 0 to 7 days Means ± standard error | Food consumption from 7 to 14 days Means ± standard error | Food consumption from 14 to 21 days Means ± standard error | Food consumption from 21 to 28 days Means ± standard error | Food consumption from 28 to 35 days Means ± standard error |
|---|---|---|---|---|---|
| Negative Control | 107 ± 1.01 [a] | 120 ± 1.27 [a] | 134 ± 5.72 [a] | 141 ± 3.44 [a] | 165 ± 3.19 [a] |
| Positive control DON | 98 ± 4.75 [a] | 109 ± 4.84 [a] | 109 ± 5.41 [b] | 121 ± 4.83 [b] | 132 ± 3.10 [b] |
| Desafío Zeotri B2 + DON | 103 ± 2.39 [a] | 119 ± 1.75 [a] | 126 ± 1.71 [a] | 137 ± 2.12 [a] | 142 ± 4.10 [b] |

Averages with different letters are statistically significant for $p < 0.05$.

The experimental results obtained show that in the DON present in the diet of the positive control group, it affected the consumption of food. The effect of DON was manifested from the third week of food consumption. The same happened in the challenge group ZB2, but to a lesser degree.

The levels of inclusion of DON in this experiment (12,000 ppb) affected the consumption of food and therefore the weight gain. These results showed statistically significant differences of these parameters between the groups.

The ZB2 mycotoxin adsorbent at a dose of 1.5 kg/T was able to decrease the effects of 12,000 ppb of DON with statistical differences against the positive control group, in the parameters evaluated.

Example 4

In Vivo Evaluation in Rats with a Mycotoxin Adsorbent of the Invention Designed to Adsorb Vomitoxin (or Deoxynivalenol) at a Higher Dose of Inclusion A second experiment was carried out with rats to evaluate the effectiveness of the adsorbent at a dose slightly higher than 2 kg/T, with a DON contamination of 12.5 ppm.

In the experiment, we used 60 freshly weaned male Sprague Dawley rats distributed in 3 treatments. A week of adaptation of the rats was also considered and the experiment lasted 35 days. A rat was used as a repetition.

The dose of the mycotoxin adsorbent of the present invention (ZB2) as mentioned, was 2 kg/T of feed and the contamination level of DON was 12.5 ppm, but in addition there was a level of contamination of Zearalenone of 10.2 ppm. The results are presented in table 7.

It is observed that the mycotoxin adsorbent of the invention, Zeotri B2, allowed a protection based on the surprisingly 59.5% weight gain, with statistical difference.

Example 5

In Vivo Evaluation of the Mycotoxin Adsorbent of the Invention Against the Adverse Effects of 1.8 ppm of T-2 Toxin from a Culture of *Fusarium Sporotrichioides*, in Broilers in the Growth Phase (Days 1 to 28 of Age)

In order to have information on the efficacy of the mycotoxin adsorbent described here, in poultry farming, an experiment was carried out with broiler chicken, using food contaminated with T2 toxin, another trichothecene.

We used 112 1-day-old chickens, distributed in 4 treatments of 4 repetitions with 7 chickens per repetition. Table 7 below shows the distribution of the treatments and the level of contamination with Toxin T2, which was of the order of 1900 ppb. The mycotoxin adsorbent of the invention was used at 2 kg/T. The experiment lasted 28 days and the base food was commercial.

TABLE 8

Design of the experiment with Toxin T2 and Zeotri B2.

| Treatment | Zeotri B2 (g/kg) | Toxin T-2 (µg/kg) |
|---|---|---|
| Negative Control | 0 | 0 |
| innocuity | 2 | 0 |
| Positive Control | 0 | 1900 |
| Challenge Zeotri | 2 | 1825 |

At the end of the experimental period, the chickens were weighed to calculate the weight gain as well as the feed conversion. Table 9 presents the final results.

TABLE 7

Initial and final weights of the rats after 35 days of experimentation, as well as data on weight gain, feed consumption and feed conversion.

| Treatments | Weight in g | | Gain of | Conversion | Consumption |
| | Stocks | Final | weight | food | food |
| | Means ± Standard error | Means ± Standard error | Means ± Standard error | Means ± Standard error | Means ± Standard error |
|---|---|---|---|---|---|
| Negative Control | 85 ± 2.67 [a] | 210 ± 9.67 [a] | 125 ± 9.24 [a] | 4.61 ± 0.172 [a] | 576 ± 25.1 [a] |
| Positive Control DON | 86 ± 1.78 [a] | 169 ± 3.69 [b] | 83 ± 3.45 [b] | 6.15 ± 0.287 [b] | 511 ± 5.71 [b] |
| Challenge Zeotri B2 + DON | 88 ± 1.91 [a] | 196 ± 7.40 [a] | 108 ± 6.40 [ab] | 5.62 ± 0.406 [b] | 607 ± 5.73 [a] |

Averages with different letters are statistically significant for $p < 0.05$.

TABLE 9

Initial and final weights of chickens after 28 days of experimentation, as well as data on weight gain, feed consumption and feed conversion.

| Treatments | Weight in g | | Gain of | Conversion | Consumption |
|---|---|---|---|---|---|
| | Initial Means ± standard error | Final Means ± standard error | weight Means ± standard error | food Means ± standard error | of food Means ± standard error |
| Negative control | 47 ± 0.52 [a] | 1525 ± 21.11 [a] | 1478 ± 21.03 [a] | 1.44 ± 0.022 [a] | 2126 ± 19.1 [a] |
| Safety | 47 ± 0.51 [a] | 1541 ± 20.36 [a] | 1494 ± 20.19 [a] | 1.47 ± 0.025 [a] | 2197 ± 50.4 [a] |
| Positive Control Toxin T-2 | 47 ± 0.52 [a] | 1418 ± 28.44 [b] | 1371 ± 28.44 [b] | 1.51 ± 0.045 [a] | 2076 ± 100 [a] |
| Challenge Zeotri | 47 ± 0.51 [a] | 1488 ± 19.49 [ab] | 1441 ± 19.38 [ab] | 1.45 ± 0.019 [a] | 2092 ± 20.6 [a] |

Averages with different letters are statistically significant for $p < 0.05$.

From this experiment it is observed that the mycotoxin adsorbent of the invention offered a good protection with statistical difference against the negative effect of Toxin T2.

It is noted that in relation to this date, the best method known to the applicant to carry out the aforementioned invention is that which is clear from the present description of the invention.

We claim:

1. A mycotoxin adsorbent characterized in that it comprises an aluminosilicate organically modified with a betaine derivative of formula (I) or with a salt of said derivative:

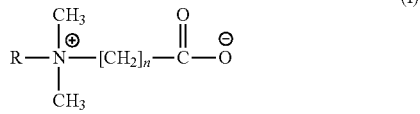

(I)

wherein R represents alkyl having 1 to 12 carbon atoms and n is 1 to 12.

2. The mycotoxin adsorbent according to claim 1, wherein the aluminosilicate is a tectosilicate, a phyllosilicate or a mixture of both.

3. The mycotoxin adsorbent according to claim 2, wherein the aluminosilicate has a cation exchange capacity of at least 20 milliequivalents per 100 grams of material.

4. An animal feed additive characterized in that it comprises the mycotoxin adsorbent according to claim 2.

5. A balanced feed formulation for animals characterized in that it comprises the mycotoxin adsorbent according to claim 2.

6. The mycotoxin adsorbent according to claim 1, wherein the betaine derivative has the formula (Ia):

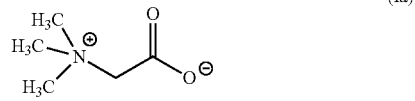

(Ia)

7. The mycotoxin adsorbent according to claim 6, wherein the aluminosilicate has a cation exchange capacity of at least 20 milliequivalents per 100 grams of material.

8. An animal feed additive characterized in that it comprises the mycotoxin adsorbent according to claim 6.

9. A balanced feed formulation for animals characterized in that it comprises the mycotoxin adsorbent according to claim 6.

10. The mycotoxin adsorbent according to claim 1, wherein the salt of the betaine derivative has the formula (Ib):

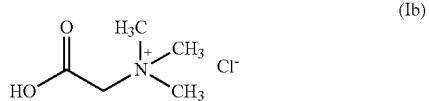

(Ib)

11. The mycotoxin adsorbent according to claim 10, wherein the aluminosilicate has a cation exchange capacity of at least 20 milliequivalents per 100 grams of material.

12. An animal feed additive characterized in that it comprises the mycotoxin adsorbent according to claim 10.

13. A balanced feed formulation for animals characterized in that it comprises the mycotoxin adsorbent according to claim 10.

14. The mycotoxin adsorbent according to claim 1, wherein the aluminosilicate has a cation exchange capacity of at least 20 milliequivalents per 100 grams of material.

15. The mycotoxin adsorbent according to claim 1, wherein the aluminosilicate has a cation exchange capacity of 55 milliequivalents per 100 grams of material.

16. The mycotoxin adsorbent according to claim 1, wherein the betaine derivative or the salt of said derivative is used in a proportion of 25% to 120% of the cation exchange capacity of the aluminosilicate used.

17. An animal feed additive characterized in that it comprises the mycotoxin adsorbent according to claim 1.

18. A premix for preparing the animal feed additive according to claim 17.

19. A balanced feed formulation for animals characterized in that it comprises the mycotoxin adsorbent according to claim 1.

* * * * *